United States Patent
Hogg et al.

(10) Patent No.: US 11,452,735 B2
(45) Date of Patent: Sep. 27, 2022

(54) PHARMACEUTICAL COMBINATIONS OF ORGANO-ARSENOXIDE COMPOUNDS AND MTOR INHIBITORS

(71) Applicant: NewSouth Innovations Pty Limited, New South Wales (AU)

(72) Inventors: Philip John Hogg, Malabar (AU); Pierre Dilda, Kingsford (AU)

(73) Assignee: Newsouth Innovations PTY Limited

( * ) Notice: Subject to any disclaimer, the term of this patent is extended or adjusted under 35 U.S.C. 154(b) by 0 days.

(21) Appl. No.: 16/915,478

(22) Filed: Jun. 29, 2020

(65) Prior Publication Data

US 2020/0323887 A1    Oct. 15, 2020

Related U.S. Application Data

(62) Division of application No. 15/736,339, filed as application No. PCT/AU2015/000347 on Jun. 15, 2015, now abandoned.

(51) Int. Cl.

| | |
|---|---|
| *A61K 31/285* | (2006.01) |
| *A61P 35/00* | (2006.01) |
| *A61K 33/36* | (2006.01) |
| *A61K 31/655* | (2006.01) |
| *A61K 31/436* | (2006.01) |
| *A61K 31/675* | (2006.01) |
| *A61K 45/06* | (2006.01) |
| *A61K 31/4709* | (2006.01) |
| *A61K 31/5377* | (2006.01) |

(52) U.S. Cl.
CPC ......... *A61K 31/655* (2013.01); *A61K 31/285* (2013.01); *A61K 31/436* (2013.01); *A61K 31/4709* (2013.01); *A61K 31/5377* (2013.01); *A61K 31/675* (2013.01); *A61K 33/36* (2013.01); *A61K 45/06* (2013.01); *A61P 35/00* (2018.01)

(58) Field of Classification Search
CPC .. A61K 31/285; A61K 2300/00; A61K 33/36; A61P 35/00
See application file for complete search history.

(56) References Cited

U.S. PATENT DOCUMENTS

| | | |
|---|---|---|
| 8,268,883 B2 | 9/2012 | Hogg et al. |
| 2010/0028338 A1 | 2/2010 | Zaknoen |
| 2010/0041749 A1 | 2/2010 | Hogg et al. |

FOREIGN PATENT DOCUMENTS

WO    2008/033466 A2    3/2008

OTHER PUBLICATIONS

Tai et al., "Combination of Rad001 (everolimus) and propachlor synergistically induces apoptosis through enhanced autophagy in prostate cancer cells," Mol. Cancer Ther. Jun. 2012;11(6):1320-31. PMID: 22491797. (Year: 2012).*

(Continued)

*Primary Examiner* — Theodore R. Howell
(74) *Attorney, Agent, or Firm* — McDonnell Boehnen Hulbert & Berghoff LLP

(57) ABSTRACT

The present invention relates to synergistic pharmaceutical combinations comprising organic arsenoxide compounds and mTOR inhibitors. Further, the present invention relates to the use of these pharmaceutical combinations in therapy, in particular, treatment of proliferative diseases.

10 Claims, 5 Drawing Sheets

(56) References Cited

OTHER PUBLICATIONS

Shen et al., "Dual-targeting of aberrant glucose metabolism in glioblastoma," J. Exp. Clin. Cancer Res. Feb. 5, 2015;34(1):14. PMID: 25652202. (Year: 2015).*

Minniti et al., "Chemotherapy for glioblastoma: current treatment and future perspectives for cytotoxic and targeted agents," Anticancer Res. Dec. 2009;29(12):5171-84. PMID: 20044633. (Year: 2009).*

Beloueche-Babari et al. (2013). Acute tumour response to the MEK1/2 inhibitor selumetinib (AZD6244, ARRY-142886) evaluated by non-invasive diffusion-weighted MRI. Br J Cancer 109, 1562-1569.

Chou, T (2010) Drug combination studies and their synergy quantification using the Chou-Talalay method. Cancer Res. 70(2) 440-446.

Dilda et al. (2009). Optimization of the antitumor efficacy of a synthetic mitochondrial toxin by increasing the residence time in the cytosol. J Med Chem 52, 6209-6216.

Klionsky et al. (2012). Guidelines for the use and interpretation of assays for monitoring autophagy. Autophagy 8, 445-544.

Lena et al. (2009). Drugs targeting the mitochondrial pore act as cytotoxic and cytostatic agents in temozolomide-resistant glioma cells. Journal of translational medicine 7, 13.

Park et al. (2012). The tumour metabolism inhibitors GSAO and PENAO react with cysteines 57 and 257 of mitochondrial adenine nucleotide translocase. Cancer cell international 12, 11.

Ramsay at al. (2011). Mitochondrial metabolism inhibitors for cancer therapy. Pharm Res 28, 2731-2744.

Roberts and Miyamoto (2015) Hexokinase II integrates energy metabolism and cellular protection: Akting on mitochondria and TORCing to autophagy. Cell Death Differ 22, 248-257.

Roberts et al. (2014). Hexokinase-II positively regulates glucose starvation-induced autophagy through TORC1 inhibition. Mol Cell 53, 521-533.

Schenone et al. (2011). ATP-competitive inhibitors of mTOR: an update. Curr Med Chem 18, 2995-3014.

Tseng et al. (2010). Enhanced specific delivery and targeting of oncolytic Sindbis viral vectors by modulating vascular leakiness in tumor. Cancer Gene Ther 17, 244-255.

Zaytseva et al. (2012). mTOR inhibitors in cancer therapy. Cancer Lett 319, 1-7.

Decollogne Stephanie et al : "Alterations in the mitochondrial responses to PENAO a mechanism of resistance in ovarian cancer cells," Gynecologic Oncology, vol. 138, No. 2, Jun. 14, 2015, pp. 363-371.

Tsoli et al. Neuro-Oncology 16:i40-i59, 2014, Abstract HG-032.

* cited by examiner

PHARMACEUTICAL COMBINATIONS OF ORGANO-ARSENOXIDE COMPOUNDS AND MTOR INHIBITORS

This application is divisional of U.S. application Ser. No. 15/736,339, filed Dec. 14, 2017, which is a US national phase under 35 U.S.C. § 371 of international application PCT/AU2015/000347, filed Jun. 15, 2015, each of which is hereby incorporated by reference in its entirety.

TECHNICAL FIELD

The present invention relates to synergistic pharmaceutical combinations comprising organic arsenoxide compounds and mTOR inhibitors. Further, the present invention relates to the use of these pharmaceutical combinations in therapy, in particular, treatment of proliferative diseases.

BACKGROUND

Arsenical compounds have been used in the past as therapeutic agents for the treatment of disease. However, the inherent toxicities of arsenical compounds and their generally unfavourable therapeutic index have largely precluded their use as pharmaceutical agents. Organic arsenoxide compounds are disclosed in WO 01/21628. Such compounds are described as having antiproliferative properties useful in the therapy of proliferative diseases. WO 04/042079 discloses the use of organic arsenoxide compounds for inducing the mitochondrial permeability transmission (MPT) and also the use of such compounds for inducing apoptosis and necrosis, particularly in endothelial cells.

Further organic arsenoxide compounds are disclosed in WO2008/052279. In particular, the compound 4-(N—(S-penicllaminylacetyl)amino)phenylarsinous acid (PENAO) is disclosed in WO2008/052279. PENAO is a mitochondrial metabolism inhibitor in the final stages of Phase I clinical testing in patients with solid tumours refractory to standard therapy at three hospitals in Australia. PENAO is a cysteine mimetic trivalent arsenical that enters cells via an organic ion transporter and accumulates in the mitochondrial matrix where the arsenical moiety cross-links Cys160 and Cys257 on the matrix face of adenine nucleotide translocase (ANT), which inactivates the transporter (Dilda et al., 2009; Park et al., 2012). Its inactivation leads to partial uncoupling of oxidative phosphorylation, increase in superoxide production, proliferation arrest and ultimately apoptosis of the cell. PENAO only reacts with ANT when cells are proliferating as Cys160 and Cys257 appear to be disulphide bonded in growth quiescent cells, and so unreactive towards PENAO.

Mammalian (mechanistic) target of rapamycin (mTOR) is a serineithreonine kinase that forms two distinct complexes called mTORC1 and mTORC2. Rapamycin (sirolimus) and rapamycin analogs (rapalogs) form a complex with the small protein FKBP12, that irreversibly binds to the FKBP12-rapamycin domain of mTORC1 and inhibits its kinase activity (Zaytseva et al., 2012). Rapamycin and rapalogs are small molecule inhibitors of mTOR and a number of clinical trials evaluating the anti-cancer efficacy of rapalogs as a monotherapy or as a part of combination therapy across a wide range of cancers types are currently in progress. The rapalogs are generally well tolerated in cancer patients (Zaytseva et al., 2012). ATP-competitive inhibitors of mTOR are also being developed (Schenone et al., 2011). These inhibitors compete with ATP for binding to the active site of the kinase.

There is a need for improved therapies for treating proliferative diseases, such as cancer (including treatment of solid tumours), and related conditions.

It has now surprisingly been found that the combination of an organo-arsenoxide compound, such as PENAO, with an mTOR inhibitor dramatically enhances the efficacy of the organo-arsenoxide compound in the treatment of proliferative diseases. The combination of the organo-arsenoxide compound and the rapamycin mTOR inhibitor has been found to act synergistically to mediate tumour cell death.

SUMMARY

In a first aspect the present invention relates to a synergistic pharmaceutical combination comprising an organo-arsenoxide compound, or a pharmaceutically acceptable salt, hydrate, solvate or prodrug thereof, and an mTOR inhibitor, or a pharmaceutically acceptable salt, hydrate, solvate or prodrug thereof. In one embodiment the organo-arsenoxide compound is PENAO. In one embodiment the mTOR inhibitor is a rapalog selected from the group consisting of everolimus, temsirolimus, deforolimus and zotarolimus.

In a second aspect the present invention relates to a pharmaceutical composition comprising an organo-arsenoxide compound, or a pharmaceutically acceptable salt, hydrate, solvate or prodrug thereof, and an mTOR inhibitor, or a pharmaceutically acceptable salt, hydrate, solvate or prodrug thereof.

In a third aspect the present invention relates to a method of treating a cellular proliferative disease in a vertebrate, the method comprising administering to the vertebrate a therapeutically effective amount of the synergistic pharmaceutical combination of the first aspect of the invention, or the pharmaceutical composition of the second aspect of the invention.

In a fourth aspect the invention relates to a method of inhibiting angiogenesis in a vertebrate, comprising administering to the vertebrate a therapeutically effective amount of the synergistic pharmaceutical combination of the first aspect of the invention, or the pharmaceutical composition of the second aspect of the invention.

In a fifth aspect the invention relates to a method of selectively inducing the Mitochondrial Permeability Transition (MPT) in proliferating cells in a vertebrate comprising administering to the vertebrate a therapeutically effective amount of the synergistic pharmaceutical combination of the first aspect of the invention, or the pharmaceutical composition of the second aspect of the invention.

In a sixth aspect the invention relates to a method of inducing apoptosis in proliferating mammalian cells, comprising administering to the vertebrate a therapeutically effective amount of the synergistic pharmaceutical combination of the first aspect of the invention, or the pharmaceutical composition of the second aspect of the invention.

In a seventh aspect the present invention relates to a method of treating a cellular proliferative disease in a vertebrate, the method comprising administering to the vertebrate a therapeutically effective amount of an organo-arsenoxide compound or a pharmaceutically acceptable salt, hydrate, solvate or prodrug thereof and an mTOR inhibitor, or a pharmaceutically acceptable salt, hydrate, solvate or prodrug thereof. In one embodiment the organo-arsenoxide compound and the mTOR inhibitor are administered simultaneously. In another embodiment the organo-arsenoxide compound is administered first, followed by the mTOR inhibitor.

In yet another aspect the present invention relates to the use of an organo-arsenoxide compound, or a pharmaceutically acceptable salt, hydrate, solvate or prodrug thereof, and an mTOR inhibitor, or a pharmaceutically acceptable salt, hydrate, solvate or prodrug thereof, for the manufacture of a medicament for the treatment of a cellular proliferative disease.

In one embodiment of the aspects of the invention the organo-arsenoxide compound is PENAO. In one embodiment of the aspects of the invention the mTOR inhibitor is a rapalog selected from the group consisting of everolimus, temsirolimus, deforolimus and zotarolimus. In one embodiment of the aspects of the invention the cellular proliferative disease is a solid tumour.

Definitions

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

The terms "synergy", "synergistic", "synergistic effect" and "synergistic combination" as used herein refers to a mixture of two or more discrete agents which, when combined, display a degree of anticancer activity, such as anti-proliferative activity or cytotoxicity etc., which is greater than the expected additive effect of said agents. The terms also refer to the combined effect of administering an amount of one therapeutic agent that, when administered alone, produces no significant response but, when administered in combination with another therapeutic compound, produces an overall response that is significantly greater than that produced by the second compound alone. CompuSyn software was utilised to calculate combination index (CI) values for drug combinations. A CI of less than 1 is indicative of a synergistic effect in drug combinations, a CI of 1 is indicative of an additive effect in drug combinations and a CI of greater than 1 is indicative of an antagonism in drug combinations (Chou, 2010).

Throughout this specification, unless the context requires otherwise, the term "combination" refers to either a fixed combination in one unit dosage form, or a non-fixed combination (or kit of parts) for the combined administration where the compound and a combination partner (e.g. another drug or therapeutic agent) are administered independently at the same time or separately within time intervals, especially where these time intervals allow that the combination partners show a co-operative, e.g. synergistic effect. The term "combined administration" as used herein is meant to encompass administration of the selected combination partners to a single subject in need thereof and are intended to include treatment regimens in which the agents are not necessarily administered by the same route of administration or at the same time.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

As used herein, the term "$C_{1-3}$ alkyl group" includes within its meaning monovalent ("alkyl") and divalent ("alkylene") straight chain or branched chain saturated aliphatic groups having from 1 to 3 carbon atoms. Thus, for example, the term $C_{1-3}$ alkyl includes methyl, ethyl, 1-propyl, and isopropyl.

The term "alkoxy" as used herein refers to straight chain or branched alkyloxy (i.e., O-alkyl) groups, wherein alkyl is as defined above. Examples of alkoxy groups include methoxy, ethoxy, n-propoxy, and isopropoxy.

The term "amino" as used herein refers to groups of the form —$NR^{a}R^{b}$ wherein $R^{a}$ and $R^{b}$ are individually selected from hydrogen, optionally substituted ($C_{1-4}$)alkyl, optionally substituted ($C_{2-4}$)alkenyl, optionally substituted ($C_{2-4}$) alkynyl, optionally substituted ($C_{6-10}$)aryl and optionally substituted aralkyl groups, such as benzyl. The amino group may be a primary, secondary or tertiary amino group.

The term "amino acid" as used herein includes naturally and non-naturally occurring amino acids, as well as substituted variants thereof. The term "amino acid" therefore encompasses, for example, $\alpha$, $\beta$, and $\gamma$-amino acids. $\alpha$-Amino acids are particularly preferred. The (L) and (D) forms of amino acids are also included in the scope of the term "amino acid". (L)-amino acids are a preferred form. For example, the term "amino acid" includes within its scope glycine, alanine, valine, leucine, isoleucine, methionine, proline, phenylalanine, tryptophan, serine, threonine, cysteine, tyrosine, asparagine, glutamine, aspartic acid, glutamic acid, lysine, arginine, histidine, $\alpha$-amino-$\beta$-hydroxyisovaleric acid and penicillamine. The backbone of the amino acid residue may be substituted with one or more groups independently selected from ($C_{1-6}$)alkyl, halogen, hydroxy, hydroxy($C_{1-6}$)alkyl, aryl, e.g., phenyl, aryl($C_{1-3}$) alkyl, e.g., benzyl, and ($C_{3-6}$)cycloalkyl.

In the context of this specification the term "arsenoxide" is synonymous with "arsinous acid" and refers to the moiety $As(OH)_{2}$, which may also be represented as As=O.

The term "halogen" or variants such as "halide" or "halo" as used herein refers to fluorine, chlorine, bromine and iodine.

The term "optionally substituted" as used herein means the group to which this term refers may be unsubstituted, or may be substituted with one or more groups independently selected from alkyl, alkenyl, alkynyl, cycloalkyl, cycloalkenyl, heterocycloalkyl, halo, haloalkyl, haloalkynyl, hydroxyl, hydroxyalkyl, alkoxy, thioalkoxy, alkenyloxy, haloalkoxy, haloalkenyloxy, $NO_{2}$, nitroalkyl, nitroalkenyl, nitroalkynyl, nitroheterocyclyl, alkylamino, dialkylamino, alkenylamino, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphono and phosphinyl, aryl, heteroaryl, alkylaryl, aralkyl, alkylheteroaryl, cyano, cyanate, isocyanate, $CO_{2}H$, $CO_{2}$alkyl, $C(O)NH_{2}$, —C(O)

NH(alkyl), and —C(O)N(alkyl)$_2$. In one embodiment substituents include $C_{1-3}$ alkyl, $C_{1-3}$ alkoxy, —CH$_2$—($C_{1-3}$) alkoxy, $C_{6-10}$ aryl, —CH$_2$-phenyl, halo, hydroxyl, hydroxy ($C_{1-3}$)alkyl (e.g., CH$_2$OH), and halo($C_{1-3}$)alkyl (e.g., CF$_3$, CH$_2$CF$_3$). Particularly preferred substituents include $C_{1-3}$ alkyl, $C_{1-3}$ alkoxy, halo, hydroxyl, hydroxy($C_{1-3}$)alkyl (e.g., CH$_2$OH), and halo($C_{1-3}$)alkyl (e.g., CF$_3$, CH$_2$CF$_3$). In one embodiment the optional substituent is $C_{1-3}$ alkyl, $C_{1-3}$ alkoxy, halo, hydroxyl or hydroxy($C_{1-3}$)alkyl (e.g., CH$_2$OH).

In the context of this specification the term "administering" and variations of that term including "administer" and "administration", includes contacting, applying, delivering or providing a compound or composition of the invention to an organism, or a surface by any appropriate means.

In the context of this specification, the term "vertebrate" includes humans and individuals of any species of social, economic or research importance including but not limited to members of the genus ovine, bovine, equine, porcine, feline, canine, primates (including human and non-human primates), rodents, murine, caprine, leporine, and avian. The vertebrate may be a human.

In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the term "effective amount" includes within its meaning a sufficient but non-toxic amount of a compound or composition of the invention to provide a desired effect. Thus, the term "therapeutically effective amount" includes within its meaning a sufficient but non-toxic amount of a compound or composition of the invention to provide the desired therapeutic effect. The exact amount required will vary from subject to subject depending on factors such as the species being treated, the sex, age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

DETAILED DESCRIPTION

Figure 1:
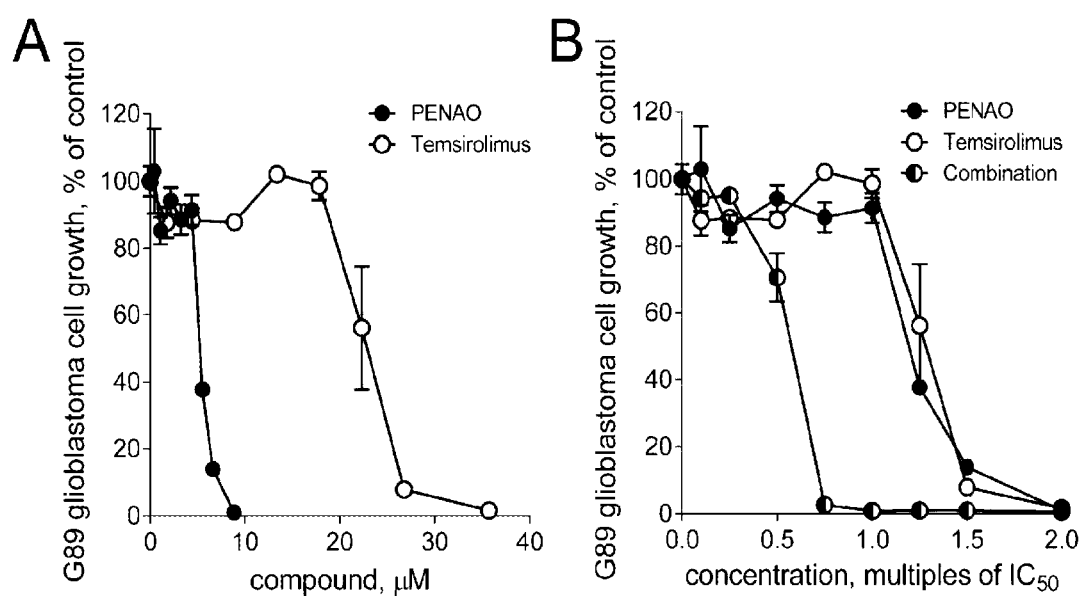
FIG. 1. Treatment of tumour cells with PENAO and mTORC1 rapalog inhibitors results in strong synergistic effects on cell proliferation. A. G89 cells were seeded in 96-well plates, allowed to adhere for 24 h then treated with PENAO or temsirolimus for 72 h. Viable cells were determined using the vital dye, MTT, and the results expressed as % of viable cells relative to untreated controls. Data points and errors are the mean and range of duplicate determinations. The result is representative of two experiments. B. Drug concentrations employed are multiples of IC$_{50}$ values for proliferation arrest in a 72 h assay (see Table 1). The combination index for G89 cells is 0.52±0.13, which is indicative of strong synergistic effect (see Table 2). Data points and errors are the mean and range of duplicate determinations. The result is representative of two experiments.

The present invention relates to synergistic pharmaceutical combinations of organic arsenoxide compounds, including PENAO, and mammalian (mechanistic) target of rapamycin (mTOR) inhibitors.

It has surprisingly been found that the rapalog inhibitors of mTORC1 combine very effectively with PENAO to trigger tumour cell death in mice. The combination effectively ablates mTOR protein in tumour cells. Importantly, combination therapy at near maximal tolerated doses of the drugs is well tolerated in mice with no signs or symptoms of toxicity.

Organo-Arsenoxide Compounds

In one embodiment of the synergistic pharmaceutical combinations of the present invention the organo-arsenoxide compound comprises an optionally substituted amino acid moiety linked via a linker group to a phenylarsenoxide group.

Organo-arsenoxide compounds in accordance with the present invention have a substituted or unsubstituted amino acid moiety. Examples of amino acid moieties include cysteinyl, substituted cysteinyl, for example penicillaminyl (also known as β,β-dimethylcysteinyl or 3-mercaptovalinyl), optionally substituted alaninyl, optionally substituted mercaptoalaninyl, optionally substituted valinyl, optionally substituted 4-mercaptovalinyl, optionally substituted leucinyl, optionally substituted 3- or 4-, or 5-mercaptoleucinyl, optionally substituted isoleucinyl, or optionally substituted 3-, 4- or 5-isoleucinyl. In a preferred embodiment of the invention the amino acid moiety is β,β-dimethycysteinyl ("penicillaminyl"). In another embodiment of the invention the amino acid moiety is (S)-penicillaminyl. In another embodiment of the invention the amino acid moiety is cysteinyl. The amino acid moiety may have (L), (D), (R) or (S) configuration. Optional substituents include $C_{1-3}$ alkyl, cyclopropyl, $C_{1-3}$ alkoxy, —$CH_2$—$(C_{1-3})$alkoxy, $C_{6-10}$ aryl, —$CH_2$-phenyl, halo, hydroxyl, hydroxy$(C_{1-3})$alkyl, and halo-$(C_{1-3})$alkyl, e.g., $CF_3$, $CH_2CF_3$. In preferred embodiments the optional substituents are independently selected from hydroxyl, methoxy, halo, methyl, ethyl, propyl, cyclopropyl, $CH_2OH$ and $CF_3$.

The linker group of the organo-arsenoxide compounds in accordance with the present invention is a substituted or unsubstituted acetamido group. In one embodiment the linker group is an unsubstituted acetamido group.

In one embodiment of the synergistic pharmaceutical combinations of the present invention the organo-arsenoxide compound is of formula (I):

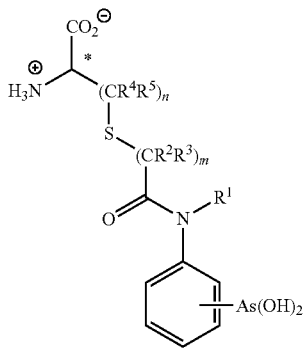

(I)

wherein the $As(OH)_2$ group is para- to the N-atom on the phenyl ring;

$R^1$ is selected from hydrogen and $C_{1-3}$ alkyl;

$R^2$ and $R^3$ may be the same or different and are independently selected from hydrogen and optionally substituted $C_{1-3}$ alkyl;

$R^4$ and $R^3$ may be the same or different and are independently selected from hydrogen and optionally substituted $C_{1-3}$ alkyl;

m is 1;

n is 1;

* indicates a chiral carbon atom; and wherein each optional substituent is independently $C_{1-3}$ alkyl, $C_{1-3}$ alkoxy, halo, hydroxyl, or hydroxy$(C_{1-3})$alkyl;

salts, enantiomers and racemates thereof.

The stereochemistry at the chiral atom indicated by * in formula (I) may be (R) or (S). The present invention includes enantiomerically pure forms of compounds of formula (I), mixtures of enantiomers in any ratio, as well as racemates. In one embodiment of the invention the stereochemistry at the chiral atom indicated by * in formula (I) is (R). In another embodiment the invention the stereochemistry at the chiral atom indicated by * in formula (I) is (S).

Preferred embodiments of the compounds of general formula (I) are described below. It should be understood that any one or more of the embodiment(s) disclosed herein may be combined with any other embodiment(s), including preferred embodiment(s).

In one embodiment $R^1$ is selected from hydrogen and $C_{1-3}$alkyl. $R^1$ may be hydrogen, methyl or ethyl. In one embodiment $R^1$ is hydrogen.

In one embodiment $R^2$ and $R^3$ may be the same or different. $R^2$ and $R^3$ may be independently selected from hydrogen, and optionally substituted $C_{1-3}$ alkyl. In one embodiment $R^2$ and $R^3$ are independently selected from hydrogen, methyl, ethyl, hydroxymethyl and $CF_3$. In a further embodiment $R^2$ and $R^3$ are independently selected from hydrogen, $C_{1-3}$ alkyl, hydroxy$(C_{1-3})$alkyl and halo $(C_{1-3})$alkyl. In another embodiment $R^2$ and $R^3$ may be independently selected from hydrogen, methyl and ethyl. In another embodiment $R^2$ is methyl and $R^3$ is hydrogen. In another embodiment $R^2$ and $R^3$ are both hydrogen.

In one embodiment $R^4$ and $R^5$ may be the same or different and are independently selected from hydrogen and optionally substituted $C_{1-3}$ alkyl. In one embodiment $R^4$ and $R^5$ are independently selected from hydrogen, $C_{1-3}$ alkyl, hydroxy-$(C_{1-3})$alkyl and halo$(C_{1-3})$alkyl. In another embodiment $R^4$ and $R^5$ may be independently selected from hydrogen, methyl, ethyl and $CH_2OH$. In another embodiment $R^4$ is methyl or ethyl and $R^5$ is hydrogen or methyl. In another embodiment $R^4$ is methyl and $R^5$ is hydrogen. In another embodiment $R^4$ and $R^5$ are both hydrogen. In another embodiment $R^4$ and $R^5$ are both methyl.

In one embodiment the optional substituent is independently $C_{1-3}$ alkyl, $C_{1-3}$ alkoxy, halo, hydroxyl, or hydroxy $(C_{1-3})$alkyl In one embodiment the optional substituents are independently selected from hydroxyl, methoxy, halo, methyl, ethyl, propyl, cyclopropyl, and $CH_2OH$. In one embodiment there are no optional substituents.

In one embodiment of the organo-arsenoxide compounds of Formula (I) the $As(OH)_2$ group is para- to the N-atom on the phenyl ring; $R^1$ is hydrogen or methyl; $R^2$ and $R^3$ are independently selected from hydrogen, $C_{1-3}$ alkyl, hydroxy $(C_{1-3})$alkyl and halo$(C_{1-3})$alkyl; $R^4$ and $R^5$ are independently selected from hydrogen, $C_{1-3}$ alkyl, hydroxy$(C_{1-3})$alkyl and halo$(C_{1-3})$alkyl; m is 1; and n is 1.

In another embodiment of the organo-arsenoxide compounds of Formula (I) the $As(OH)_2$ group is para- to the N-atom on the phenyl ring; $R^1$ is hydrogen; $R^2$ is hydrogen or methyl; $R^3$ is hydrogen; $R^4$ is hydrogen or methyl; $R^5$ is hydrogen or methyl; m is 1; and n is 1.

In one embodiment the organo-arsenoxide compound has the following structural formula

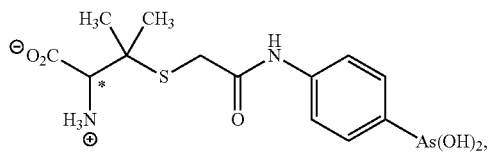

or a salt, an enantiomer or racemate thereof. This compound is referred to herein as "Penicillamine-arsenoxide" or "PENAO". In one embodiment the stereochemistry at the chiral carbon denoted * is (S).

In one embodiment of the synergistic pharmaceutical combinations of the invention the organo-arsenoxide compound of formula (I) is (S)-Penicillamine-arsenoxide. In another embodiment the compound of formula (I) is (R)-Penicillamine-arsenoxide. In another embodiment the compound of formula (I) comprises a mixture of (R) and (S) enantiomers of Penicillamine-arsenoxide. In another embodiment, the mixture of (R) and (S) enantiomers of Penicillamine-arsenoxide is a racemic mixture.

mTOR Inhibitors

Mammalian (mechanistic) target of rapamycin (mTOR) inhibitors of the present invention include rapamycin (sirolimus) and rapamycin analogs (rapalogs). Non-limiting examples of rapalogs include everolimus, temsirolimus, deforolimus and zotarolimus. mTOR inhibitors also include non-rapamycin inhibitors such as AXD8055, a selective ATP-competitive mTOR kinase inhibitor, and BEZ235, a dual PI3K and mTOR inhibitor. In a preferred embodiment of the synergistic pharmaceutical combinations of the present invention the mTOR inhibitor is a rapalog.

In one embodiment of the synergistic pharmaceutical combinations of the present invention the mTOR inhibitor is selected from the group consisting of everolimius, temsirolimus, deforolimus and zotarolimus. In another embodiment of the synergistic pharmaceutical combinations of the present invention the mTOR inhibitor is selected from the group consisting of everolimius, temsirolimus and deforolimus. In a further embodiment of the synergistic pharmaceutical combinations of the present invention the mTOR inhibitor is everolimus or temsirolimus. In another embodiment of the synergistic pharmaceutical combinations of the present invention the mTOR inhibitor is everolimus. In a further embodiment of the synergistic pharmaceutical combinations of the present invention the mTOR inhibitor is temsirolimus.

Synergistic Pharmaceutical Combinations

In one aspect the present invention relates to a synergistic pharmaceutical combination comprising an organo-arsenoxide compound, or a pharmaceutically acceptable salt, hydrate, solvate or prodrug thereof, and an mTOR inhibitor, or a pharmaceutically acceptable salt, hydrate, solvate or prodrug thereof. Such a combination may be for simultaneous, separate or sequential administration. Such a combination may be useful in the treatment of proliferative diseases, including solid tumours.

In one embodiment of the synergistic pharmaceutical combination of the present invention the organo-arsenoxide compound and the mTOR inhibitor are present in a single dosage form. In another embodiment of the synergistic pharmaceutical combination of the present invention the organo-arsenoxide compound and the mTOR inhibitor are present in separate dosage forms.

In one embodiment the synergistic pharmaceutical combination comprises an organo-arsenoxide compound of formula (I), or a pharmaceutically acceptable salt, hydrate, solvate or prodrug thereof and an mTOR inhibitor, or a pharmaceutically acceptable salt, hydrate, solvate or prodrug thereof.

In another embodiment the synergistic pharmaceutical combination comprises the organo-arsenoxide compound PENAO, or a pharmaceutically acceptable salt thereof and an mTOR inhibitor, or a pharmaceutically acceptable salt, hydrate, solvate or prodrug thereof. In a further embodiment of the synergistic pharmaceutical combinations of the present invention the organo-arsenoxide compound is 4-(N—(S-penicllaminylacetyl)amino)phenylarsinous acid (PENAO), or a pharmaceutically acceptable salt thereof, and the mTOR inhibitor is a rapalog.

In a further embodiment the synergistic pharmaceutical combination comprises the organo-arsenoxide compound PENAO, or a pharmaceutically acceptable salt thereof and a rapalog mTOR inhibitor. In another embodiment the synergistic pharmaceutical combination comprises PENAO, or a pharmaceutically acceptable salt thereof, and a rapalog selected from the group consisting of everolimus, temsirolimus, deforolimus and zotarolimus. In a further embodiment the synergistic pharmaceutical combination comprises PENAO, or a pharmaceutically acceptable salt thereof, and a rapalog selected from the group consisting of everolimus and temsirolimus. In another embodiment the synergistic pharmaceutical combination comprises PENAO, or a pharmaceutically acceptable salt thereof, and everolimus. In a further embodiment the synergistic pharmaceutical combination comprises PENAO, or a pharmaceutically acceptable salt thereof, and temsirolimus.

The combination therapy provide herein may be useful for improving the efficacy and/or reducing the side effects of currently available cancer therapies for individuals who do not respond to such therapies.

In one embodiment the combination of an organo-arsenoxide compound, such as PENAO, with an mTOR inhibitor, such as a rapalog dramatically enhances the efficacy of the organo-arsenoxide compound in the treatment of proliferative diseases. In one embodiment the therapeutic efficacy of the organo-arsenoxide compound may be enhanced by about 10% to about 2000%. In one embodiment the therapeutic effect may be enhanced by about 10%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000%, 1050%, 1100%, 1150%, 1200%, 1250%, 1300%, 1350%, 1400%, 1450%, 1500%, 1550%, 1600%, 1650%, 1700%, 1750%, 1800%, 1850%, 1900%, 1950% or about 2000%.

In one embodiment of the pharmaceutical combinations of the present invention the organo-arsenoxide compound and the mTOR inhibitor have a combination index (CI) of less than 1. A CI of less than 1 is indicative of synergistic effect in drug combinations. In another embodiment of the pharmaceutical combinations of the present invention the organo-arsenoxide compound and the mTOR inhibitor have a CI of less than 0.8. In a further embodiment of the pharmaceutical combinations of the present invention the organo-arsenoxide compound and the mTOR inhibitor have a CI of less than 0.7. In another embodiment of the pharmaceutical combinations of the present invention the organo-arsenoxide compound and the mTOR inhibitor have a CI between 0.5 and 0.7. In a further embodiment of the pharmaceutical combinations of the present invention the organo-arsenoxide compound and the mTOR inhibitor have a CI between about 0.5 and about 0.8.

A further aspect of the invention provides for a pharmaceutical composition comprising an organo-arsenoxide compound, or a pharmaceutically acceptable salt, hydrate, solvate or prodrug thereof, and an mTOR inhibitor, or a pharmaceutically acceptable salt, hydrate, solvate or prodrug thereof. In one embodiment of the pharmaceutical composition of the present invention the organo-arsenoxide compound is PENAO, or a pharmaceutically acceptable salt thereof, and the mTOR inhibitor is a rapalog selected from the group consisting of everolimus, temsirolimus, deforolimus and zotarolimus.

Therapeutic Application(s)

Compounds of formula (I) as disclosed herein, such as PENAO, and pharmaceutically acceptable salts and hydrates thereof, are capable of binding to cysteine residues of mitochondrial Adenine Nucleotide Translocator (ANT) in proliferating endothelial cells thereby inducing the Mitochondrial Permeability Transition (MPT). Accordingly, compounds of formula (I) according to the present invention may lead to proliferation arrest and cell death. Advantageously, compounds of formula (I) may be selective inhibitors of endothelial cell proliferation. For example, compounds of formula (I) may be selective inhibitors of endothelial cell proliferation compared to tumour cells. Compounds of formula (I) therefore may be useful in the treatment of proliferative diseases.

Therefore, in other aspects of the invention the synergistic pharmaceutical combination of an organo-arsenoxide compound and an mTOR inhibitor may be useful in the treatment of proliferative diseases. Accordingly, another embodiment of the invention relates to a method of treating a cellular proliferative disease in a vertebrate, the method comprising administering to the vertebrate a therapeutically effective amount of a synergistic pharmaceutical combination of the present invention. The cells may be endothelial cells. The vertebrate may be a mammal, such as a human.

In accordance with the present invention the organo-arsenoxide compound and mTOR inhibitor may be administered as a single pharmaceutical composition, as separate compositions or sequentially.

In another embodiment the present invention relates to a method of inhibiting angiogenesis in a vertebrate, comprising administering to the vertebrate an effective amount of a synergistic pharmaceutical combination of the present invention.

A further embodiment of the invention relates to a method of inducing the MPT in a vertebrate comprising administering to the vertebrate a therapeutically effective amount of a synergistic pharmaceutical combination of the present invention. Compounds of formula (I) as disclosed herein may induce the MPT by binding to cysteine residues on mitochondrial Adenine Nucleotide Translocator (ANT).

Another embodiment of the invention relates to a method of inducing apoptosis in proliferating mammalian cells, comprising administering to the mammal an apoptosis-inducing amount of a synergistic pharmaceutical combination of the present invention.

Another embodiment of the present invention relates to a method of treating a cellular proliferative disease in a vertebrate, the method comprising administering to the vertebrate a therapeutically effective amount of an organo-arsenoxide compound or a pharmaceutically acceptable salt, hydrate, solvate or prodrug thereof and an mTOR inhibitor, or a pharmaceutically acceptable salt, hydrate, solvate or prodrug thereof. In one embodiment the organo-arsenoxide compound and the mTOR inhibitor are administered simultaneously or concurrently. In a further embodiment the organo-arsenoxide compound is administered first, followed by the mTOR inhibitor. In another embodiment of the methods of the present invention PENAO and a rapalog selected from the group consisting of everolimus, temsirolimus and deforolimus are administered concurrently or simultaneously. In one embodiment PENAO and a rapalog selected from the group consisting of everolimus, temsirolimus and deforolimus act synergistically when administered concurrently. In a further embodiment of the methods of the present invention PENAO is administered first, followed by administration of a rapalog selected from the group consisting of everolimus, temsirolimus and deforolimus, to achieve a synergistic effect.

In one embodiment the present invention relates to a method of treating a cellular proliferative disease in a vertebrate, the method comprising administering to the vertebrate a therapeutically effective amount of PENAO, or a pharmaceutically acceptable salt thereof and a rapalog selected from the group consisting of everolimus, temsirolimus and deforolimus.

The present invention further relates to the use of an organo-arsenoxide compound, or a pharmaceutically acceptable salt, hydrate, solvate or prodrug thereof, and an mTOR inhibitor, or a pharmaceutically acceptable salt, hydrate, solvate or prodrug thereof, for the manufacture of a medicament for the treatment of a cellular proliferative disease. In one embodiment the invention relates to the use of PENAO, or a pharmaceutically acceptable salt thereof, and a rapalog selected from the group consisting of everolimus, temsirolimus and deforolimus for the manufacture of a medicament for the treatment of a cellular proliferative disease.

The present invention further relates to a kit comprising the pharmaceutical combination of an organo-arsenoxide compound, or a pharmaceutically acceptable salt, hydrate, solvate or prodrug thereof, and an mTOR inhibitor, or a pharmaceutically acceptable salt, hydrate, solvate or prodrug thereof.

In one embodiment the cellular proliferative disease is a solid tumour. In one embodiment the solid tumour is selected from the group consisting of lung cancer; breast cancer; colorectal cancer; anal cancer; pancreatic cancer; prostate cancer, ovarian carcinoma; liver and bile duct carcinoma; esophageal carcinoma; non-Hodgkin's lymphoma; bladder carcinoma; carcinoma of the uterus; glioma, diffuse intrinsic pontine glioma, glioblastoma, medullablastoma, and other tumours of the brain; kidney cancer; cancer of the head and neck; cancer of the stomach; testicular cancer; germ cell tumour; neuroendocrine tumour, cervical cancer; oral cancer, carcinoids of the gastrointestinal tract, breast, and other organs; signet ring cell carcinoma; mesenchymal tumours including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma or a leiomysarcoma.

In one embodiment the solid tumour is selected from the group consisting of pancreatic cancer, ovarian carcinoma and glioblastoma.

Therapeutic advantages may be realised through further combination regimens, with the addition of a third active agent. In combination therapy the respective agents may be administered simultaneously, or sequentially in any order.

Accordingly, methods of treatment according to the present invention may be applied in conjunction with conventional therapy, such as radiotherapy, chemotherapy, surgery, or other forms of medical intervention. Examples of additional chemotherapeutic agents include adriamycin, taxol, fluorouricil, melphalan, cisplatin, oxaliplatin, alpha interferon, vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide, nitrosoureas including carmustine, lomustine, semustine and streptozocin; alkyl sulfonates including busulfan; triazines including dicarbazine; ethyenimines including thiotepa and hexamethylmelamine; folic acid analogues including methotrexate; pyrimidine analogues including 5-fluorouracil, cytosine arabinoside; purine analogues including 6-mercaptopurine and 6-thioguanine; antitumour antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar, and regimens such as COMP (cyclophosphamide, vincristine, methotrexate and prednisone), etoposide, mBACOD (methotrexate, bleomycin, doxorubicin, cyclophosphamide, vincristine and dexamethasone), and PROMACE/MOPP (prednisone, methotrexate (w/leucovin rescue), doxorubicin, cyclophosphamide, taxol, etoposide/mechlorethamine, vincristine, prednisone and procarbazine).

Pharmaceutical and/or Therapeutic Formulations

Typically, for medical use, salts of the compounds of the present invention will be pharmaceutically acceptable salts; although other salts may be used in the preparation of the inventive compounds or of the pharmaceutically acceptable salt thereof. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art.

Pharmaceutically acceptable salts of compounds of formula I may be prepared by methods known to those skilled in the art, including for example, (i) by reacting a compound of formula (I) with the desired acid or base; (ii) by removing an acid- or base-labile protecting group from a suitable precursor of the compound of formula (I) or by ring-opening a suitable cyclic precursor, for example, a lactone or lactam, using the desired acid or base; or (iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

Thus, for instance, suitable pharmaceutically acceptable salts of compounds according to the present invention may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention. Suitable pharmaceutically acceptable salts of the compounds of the present invention therefore include acid addition salts.

S. M. Berge et al. describe pharmaceutically acceptable salts in detail in *J. Pharmaceutical Sciences*, 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

Convenient modes of administration include injection (subcutaneous, intravenous, etc.), oral administration, inhalation, transdermal application, topical creams or gels or powders, or rectal administration. In one embodiment, the mode of administration is parenteral. In another embodiment, the mode of administration is oral. Depending on the route of administration, the formulation and/or compound may be coated with a material to protect the compound from the action of enzymes, acids and other natural conditions which may inactivate the therapeutic activity of the compound. The compound also may be administered parenterally or intraperitoneally. The organo-arsenoxide and the mTOR inhibitors of the present invention may be administered by different modes of administration. In one embodiment the organo-arsenoxide is administered subcutaneously and the mTOR inhibitor is administered orally.

Dispersions of compounds according to the invention may also be prepared in glycerol, liquid polyethylene glycols, and mixtures thereof and in oils. Under ordinary conditions of storage and use, pharmaceutical preparations may contain a preservative to prevent the growth of microorganisms.

Pharmaceutical compositions suitable for injection include sterile aqueous solutions (where water soluble) or dispersions and sterile powders for the extemporaneous preparation of sterile injectable solutions or dispersions. Ideally, the composition is stable under the conditions of manufacture and storage and may include a preservative to stabilise the composition against the contaminating action of microorganisms such as bacteria and fungi.

The compound(s) of the invention may be administered orally, for example, with an inert diluent or an assimilable edible carrier. The compound(s) and other ingredients may also be enclosed in a hard or soft shell gelatin capsule, compressed into tablets, or incorporated directly into an individual's diet. For oral therapeutic administration, the compound(s) may be incorporated with excipients and used in the form of ingestible tablets, buccal tablets, troches, capsules, elixirs, suspensions, syrups, wafers, and the like. Suitably, such compositions and preparations may contain at least 1% by weight of active compound. The percentage of the compound(s) of formula (I) in pharmaceutical compositions and preparations may, of course, be varied and, for example, may conveniently range from about 2% to about 90%, about 5% to about 80%, about 10% to about 75%, about 15% to about 65%; about 20% to about 60%, about 25% to about 50%, about 30% to about 45%, or about 35% to about 45%, of the weight of the dosage unit. The amount of compound in therapeutically useful compositions is such that a suitable dosage will be obtained.

The language "pharmaceutically acceptable carrier" is intended to include solvents, dispersion media, coatings, anti-bacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated. Supplementary active compounds may also be incorporated into the compositions according to the present invention. It is especially advantageous to formulate parenteral compositions in dosage unit form for ease of administration and uniformity of dosage. "Dosage unit form" as used herein refers to physically discrete units suited as unitary dosages for the individual to be treated; each unit containing a predetermined quantity of compound(s) is calculated to produce the desired therapeutic effect in association with the required pharmaceutical carrier. The compound(s) may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

In one embodiment, the carrier is an orally administrable carrier.

Another form of a pharmaceutical composition is a dosage form formulated as enterically coated granules, tablets or capsules suitable for oral administration.

Also included in the scope of this invention are delayed release formulations.

Compounds of formula (I) according to the invention also may be administered in the form of a "prodrug". Suitable prodrugs include esters, phosphonate esters etc., of the compound.

In one embodiment, the compound of formula (I) may be administered by injection. In the case of injectable solutions, the carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by including various anti-bacterial and/or anti-fungal agents. Suitable agents are well known to those skilled in the art and include, for example, parabens, chlorobutanol, phenol, benzyl alcohol, ascorbic acid, thimerosal, and the like. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminium monostearate and gelatin.

Sterile injectable solutions can be prepared by incorporating the analogue in the required amount in an appropriate solvent with one or a combination of ingredients enumerated above, as required, followed by filtered sterilisation. Generally, dispersions are prepared by incorporating the analogue into a sterile vehicle which contains a basic dispersion medium and the required other ingredients from those enumerated above.

Tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the analogue, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the analogue can be incorporated into sustained-release preparations and formulations.

The pharmaceutical composition may further include a suitable buffer to minimise acid hydrolysis. Suitable buffer agents are well known to those skilled in the art and include, but are not limited to, phosphates, citrates, carbonates and mixtures thereof.

Single or multiple administrations of the compounds and/or pharmaceutical compositions according to the invention may be carried out. One skilled in the art would be able, by routine experimentation, to determine effective, non-toxic dosage levels of the compound and/or composition of the invention and an administration pattern which would be suitable for treating the diseases and/or infections to which the compounds and compositions are applicable.

Further, it will be apparent to one of ordinary skill in the art that the optimal course of treatment, such as the number of doses of the compound or composition of the invention given per day for a defined number of days, can be ascertained using convention course of treatment determination tests.

Generally, an effective dosage per 24 hours may be in the range of about 0.0001 mg to about 1000 mg per kg body weight; for example, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight.

Alternatively, an effective dosage may be up to about 500 mg/m$^2$. For example, generally, an effective dosage is expected to be in the range of about 25 to about 500 mg/m$^2$, about 25 to about 350 mg/m$^2$, about 25 to about 300 mg/m$^2$, about 25 to about 250 mg/m$^2$, about 50 to about 250 mg/m$^2$, and about 75 to about 150 mg/m$^2$.

In another embodiment, a compound of Formula (I) may be administered in an amount in the range from about 100 to about 1000 mg per day, for example, about 200 mg to about 750 mg per day, about 250 to about 500 mg per day, about 250 to about 300 mg per day, or about 270 mg to about 280 mg per day.

Compounds in accordance with the present invention may be administered as part of a therapeutic regimen with other drugs. It may be desirable to administer a combination of active compounds, for example, for the purpose of treating a particular disease or condition. Accordingly, it is within the scope of the present invention that two or more pharmaceutical compositions, at least one of which contains a compound of formula (I) according to the present invention, and at least one of which includes an mTOR inhibitor, may be combined in the form of a kit suitable for simultaneous or sequential administration of the compositions.

The invention will now be described in more detail, by way of illustration only, with respect to the following examples. The examples are intended to serve to illustrate this invention and should not be construed as limiting the generality of the disclosure of the description throughout this specification.

EXAMPLES

Example 1—Treatment of Tumour Cells with PENAO and mTORC1 Rapalog Inhibitors Results in Strong Synergistic Effects on Cell Proliferation Except otherwise mentioned, all the reagents and chemicals were from Sigma (St Louis, Mo.). PENAO was prepared as described previously (WO2008/052279). Except otherwise mentioned, cells were from ATCC (Bethesda, Va.) and all culture media, serum, antibiotics and supplements were from Invitrogen (Mulgrave, VIC, Australia). All cultures contained 20 units/mL penicillin and 20 units/mL streptomycin. AsPC1 cells (human pancreatic adenocarcinoma, derived from metastatic site, Kras mutated G12D), SKOV3 (human endometrioid ovarian cancer) and U251MG (human glioblastoma astrocytoma) cells were cultured in RPMI 1640 medium containing 10% v/v foetal bovine serum and 2 mM glutamine. Panc1 (human pancreatic adenocarcinoma, Kras mutated G12D) cells were cultured in DMEM containing 2 mM glutamine. Capan1 (human pancreatic adenocarcinoma, derived from metastatic site, Kras mutated G12V) cells were cultured in IMDM containing 20% v/v foetal bovine serum and 2 mM glutamine. MiaPaca2 cells (human pancreatic adenocarcinoma, Kras mutated G12C) were cultured in DMEM containing 10% v/v foetal bovine serum, 2.5% v/v horse serum and 2 mM glutamine. G89 (primary glioblastoma patient-derived cells, unmethylated MGMT promoter) cells were cultured using serum free media (RHB-A, Cellartis, Takara Bio Inc) with 20 ng/mL EGF and FGF on freshly pre-coated Matrigel (1:100 in phosphate-buffered saline, Falcon, Corning). Subsequent passages upon confluency is performed with twice phosphate-buffered saline (5 mL) washes, followed by 5 min with accutase (2 mL per T75 flask) that is then inactivated with trypsin inhibitor (half the volume of accutase). G89 cells were obtained from A/Prof Kerrie McDonald. All cell lines were tested negative for contamination with *Mycoplasma* spp. and maintained in a controlled environment of 5% $CO_2$ and 95% relative humidity at 37° C.

MiaPaca2, AsPC1, Panc1, Capan1, SKOV3 and U251MG cells were seeded at a density of 4×10$^3$ cells/well, and G89 cells at 1×10$^4$ cells/well, in 96-well plates. Cells were allowed to adhere for 24 h at 37° C. in a 5% $CO_2$, 95% air atmosphere and then treated with compounds (see Table 1 and FIG. 1 for details) for 72 h. Viable cells were determined using the vital dye, MTT, according to the manufacturer's instructions.

MiaPaca2 cells were seeded at a density of 4×10$^3$ cells per well in a E-Plate 96 PET to monitor real-time proliferation using the xCELLigence System RTCA MP instrument (Roche) according to the manufacturer's instructions. Cells were allowed to adhere for 24 h at 37° C. in a 5% $CO_2$, 95% air atmosphere and then treated either concurrently or sequentially with PENAO and everolimus (see FIG. 2 for details) for up to 100 h.

Results:

PENAO and the rapalog inhibitors of mTORC1 (temsirolimus, everolimus and deforolimus) act synergistically to inhibit the proliferation of different human pancreatic, ovarian and brain tumour cells in culture (Tables 1 and 2, FIG. 1). Combination indices in the range 0.52 (G89) to 0.89 (AsPC1) were observed. An index of less than 1 is indicative of synergistic effect. The ATP-competitive mTOR inhibitors, AZD8055 and BEZ235, did not exhibit any synergistic effect with PENAO, only the rapalog inhibitors.

PENAO and rapalog inhibitors of mTORC1 act synergistically to block the proliferation and induce autophagy and death of human tumour cells in culture. The ATP-competitive mTOR inhibitors do not exhibit any synergistic effect with PENAO, only the rapalog inhibitors.

Table 1. PENAO and mTORC1 Inhibitors Induce Proliferation Arrest in Cell Lines Established from Pancreatic, Ovarian and Brain Tumours.

Tumour cell lines were seeded in 96-well plates, allowed to adhere for 24 then treated with the compounds for 72 h. Viable cells were determined using the vital dye, MTT. $IC_{50}$ values for proliferation arrest are mean±SD from at least two experiments performed in triplicates. See FIG. 1A for an example of a cell proliferation result for brain G89 cells. n.d. is not determined.

| Compound | Pancreas | | | |
|---|---|---|---|---|
| | MiaPaca2 $IC_{50}$ ± SD, µM | AsPC1 $IC_{50}$ ± SD, µM | Panc1 $IC_{50}$ ± SD, µM | Capan1 $IC_{50}$ ± SD, µM |
| PENAO | 2.05 ± 0.54 | 8.98 ± 1.09 | 4.73 ± 0.96 | 9.19 ± 2.69 |
| Temsirolimus | 24.6 ± 3.1 | 19.0 ± 3.1 | 31.7 ± 0.9 | 29.2 ± 2.0 |
| Everolimus | 44.0 ± 4.0 | 23.9 ± 3.4 | 43.1 ± 0.6 | 34.3 ± 4.0 |
| Deforolimus | 56.4 ± 6.9 | 30.0 ± 5.8 | 59.3 ± 3.4 | 48.4 ± 3.5 |
| AZD8055 | 0.14 ± 0.03 | 0.01 ± 0.00 | >3 | >1 |
| BEZ235 | 0.12 ± 0.06 | 0.02 ± 0.01 | n.d. | n.d. |

| Compound | Ovary | Brain | |
|---|---|---|---|
| | Skov3 $IC_{50}$ ± SD, µM | U251MG $IC_{50}$ ± SD, µM | G89 $IC_{50}$ ± SD, µM |
| PENAO | 7.78 ± 1.30 | 3.03 ± 0.01 | 4.74 ± 0.51 |
| Temsirolimus | 20.4 ± 0.5 | 13.6 ± 0.8 | 20.4 ± 2.7 |
| Everolimus | n.d. | n.d. | n.d. |
| Deforolimus | n.d. | n.d. | n.d. |
| AZD8055 | n.d. | n.d. | n.d. |
| BEZ235 | n.d. | n.d. | n.d. |

Table 2. PENAO and mTORC Rapalog Inhibitors Synergise to Block the Proliferation of Cell Lines Established from Pancreatic, Ovarian and Brain Tumours.

Tumour cell lines were seeded in 96-well plates, allowed to adhere for 24 then treated with the compounds for 72 h, either as single agent or in a fixed ratio combination. Viable cells were determined using the vital dye, MTT. Combination index (CI) values at 50% of effective dose ($ED_{50}$) were determined using CompuSyn software. CI values are mean±SD from at least two experiments. See FIG. 1B for an example of synergy cell proliferation result for brain G89 cells. n.d. is not determined.

| Combination with PENAO | Pancreas | | | |
|---|---|---|---|---|
| | MiaPaca2 CI at $ED_{50}$ | AsPC1 CI at $ED_{50}$ | Panc1 CI at $ED_{50}$ | Capan1 CI at $ED_{50}$ |
| Temsirolimus | 0.70 ± 0.05 | 0.77 ± 0.04 | 0.68 ± 0.04 | 0.74 ± 0.07 |
| Everolimus | 0.75 ± 0.05 | 0.78 ± 0.01 | 0.59 ± 0.11 | 0.82 ± 0.06 |
| Deforolimus | 0.80 ± 0.10 | 0.89 ± 0.04 | 0.73 ± 0.01 | 0.64 ± 0.12 |
| AZD8055 | 1.26 ± 0.26 | 1.06 ± 0.17 | n.d. | n.d. |
| BEZ235 | 1.41 ± 0.18 | 1.19 ± 0.08 | n.d. | n.d. |

| Combination with PENAO | Ovary | Brain | |
|---|---|---|---|
| | Skov3 CI at $ED_{50}$ | U251MG CI at $ED_{50}$ | G89 CI at $ED_{50}$ |
| Temsirolimus | 0.74 ± 0.07 | 0.81 ± 0.06 | 0.52 ± 0.13 |
| Everolimus | n.d. | n.d. | n.d. |
| Deforolimus | n.d. | n.d. | n.d. |
| AZD8055 | n.d. | n.d. | n.d. |
| BEZ235 | n.d. | n.d. | n.d. |

Figure 2:
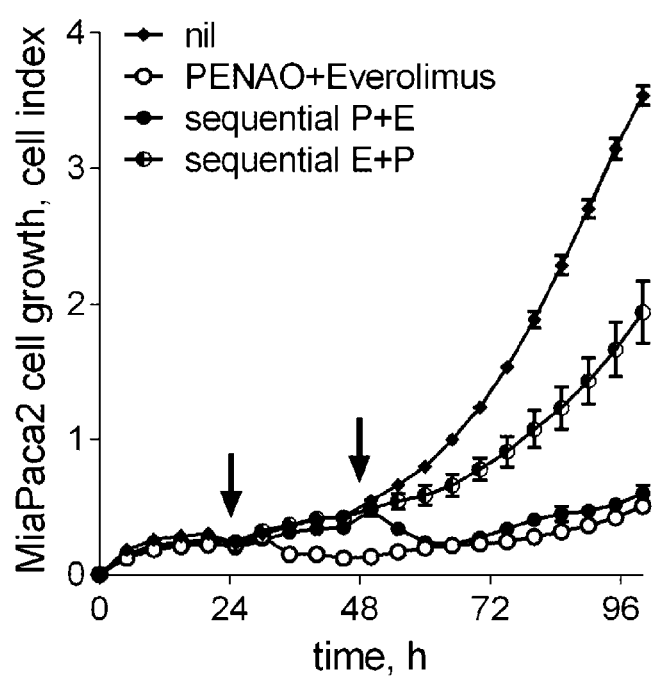
FIG. 2. The order of treatment of tumour cells with PENAO and rapalog influences the synergistic effects on proliferation. 24 h after seeding, MiaPaca2 cells were treated concurrently or sequentially (at 24 and 48 h time points) with PENAO (P, 0.75 µM) and everolimus (E, 22 µM). Cell growth was recorded every 5 h using the xCELLigence System. Data points and errors are the mean and SD of triplicate determinations. The results are representative of two experiments.

Example 2—the Order of Treatment of Tumour Cells with PENAO and Rapalog Influences the Synergistic Effects on Proliferation Addition of PENAO first followed by the rapalog (everolimus) results in synergistic inhibition of human pancreatic MiaPaca2 cell proliferation at levels comparable to when the compounds are added at the same time (FIG. 2). In contrast, the synergy is not apparent when everolimus is added before PENAO.

The order of treatment of tumour cells influences the effects on proliferation, with addition of PENAO followed by a rapalog achieving comparable synergy as when the compounds are administered concurrently. The synergy of the two compounds is not apparent when a rapalog is administered first, followed by PENAO.

Example 3—Treatment with PENAO and Rapalog Depletes Tumour Cells of mTOR and Induces Autophagy and Apoptosis Proteins from SKOV3 cell lysates were resolved by SDS-PAGE and immunoblotted with antibodies that recognise LC3B (Cell Signaling), cPARP-1 (Cell Signaling), mTOR, Akt, 3EBP1, β actin or GAPDH (Abcam). Images were acquired using an ImageQuant LAS 4000 system (GE Healthcare Life Sciences). Detection of autolysosomes was performed 24 h after compound exposure by staining for 15 min with Acridine Orange (0.25 μg/mL, Life Technologies). Images were acquired in the green (BP530-585 nm) and red (BP450-490 nm) fluorescence channels using a Zen2012 Carl-Zeiss-AxioVert.A.1 fluorescence microscope (Klionsky et al., 2012; Lena et al., 2009).

Figure 3:
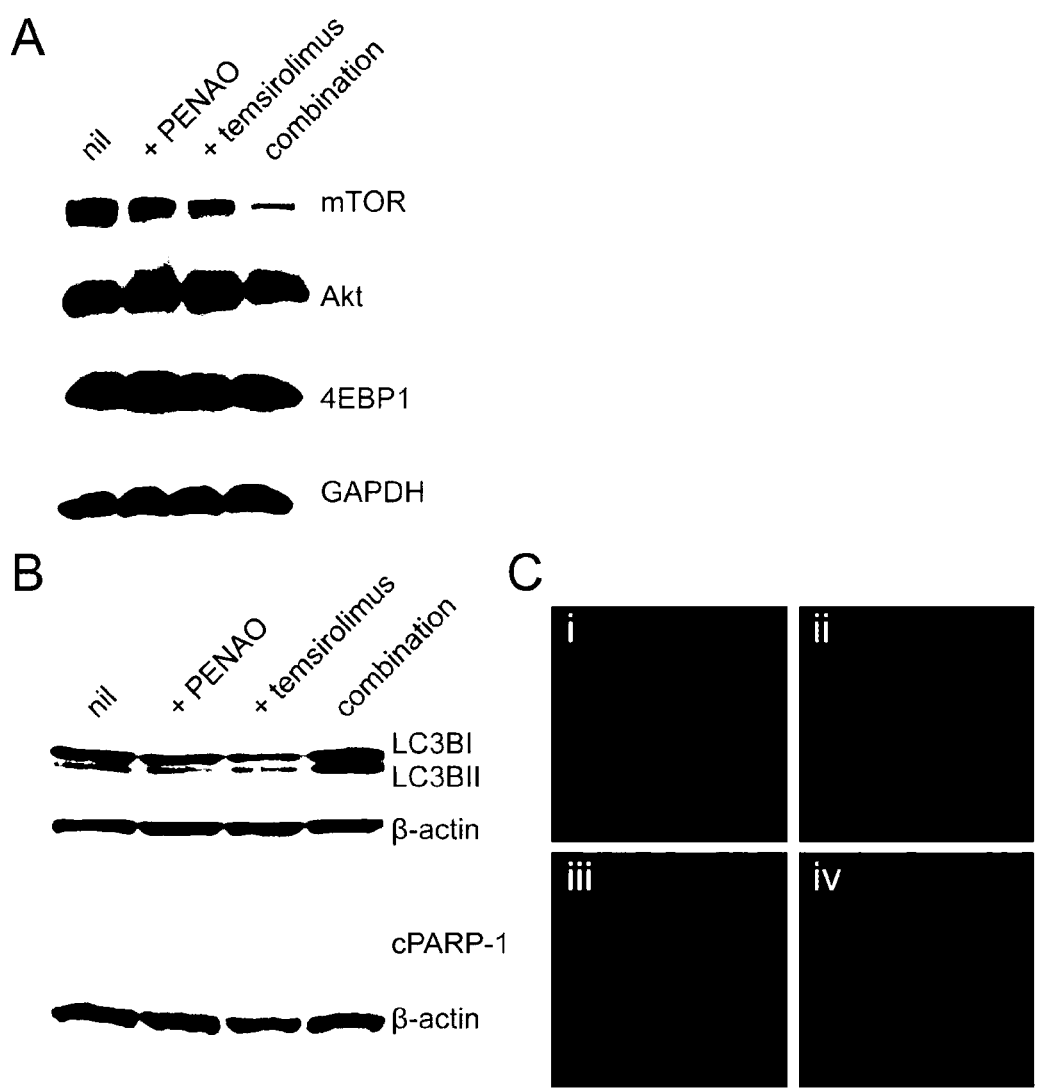
FIG. 3. Treatment with PENAO and rapalog depletes tumour cells of mTOR and induces autophagy and apoptosis. A. DIPG cells were treated with PENAO (2 µM) and/or temsirolimus (5 µM) for 48 h and lysate blotted for mTOR, Akt and 4EBP1 protein levels. Combination treatment ablates mTOR protein in the cells, but not AKT and 4EBP1. Loading control is GAPDH. The blots presented are representative of several separate experiments. B. Ovarian SKOV3 cancer cells were treated with PENAO (5 µM) and/or temsirolimus (10 µM) for 24 h and lysate blotted for autophagy (LC3BI/II) and apoptosis (cPARP-1). Loading control is β-actin. The blots presented are representative of 2 separate experiments. C. SKOV-3 cells were either untreated (i), treated with PENAO (5 µM, ii), temsirolimus (10 µM, iii) or with the combination (iv) for 24 h. An accumulation of acidic vesicles (red fluorescence) is indicative of autophagy. Images are representative fields from two separate experiments. Magnification is 400×.

Results:
Combination PENAO and rapalog treatment ablates mTOR protein in human diffuse intrinsic pontine glioma (DIPG) cells, but not other proteins in the pathway (AKT and 4EBP1) (FIG. 3A). Combination treatment of human ovarian tumour cells results in autophagy and apoptosis in the cells (FIG. 3B and FIG. 3C).

Example 4—Treatment with PENAO and Rapalog Results in Synergistic Inhibition of Tumour Growth and Tumour Necrosis in Mice Female 6-8 week old BALB/c nude mice were injected subcutaneously in the proximal midline with $4\times10^6$ pancreatic carcinoma MiaPaca2 cells. Mice bearing ~100 $mm^3$ tumours were randomized into four groups (n=8 per group) and implanted with subcutaneous Alzet micro-osmotic model 1004 pumps in the flank that delivered vehicle or 0.25 mg/kg/day PENAO. Four days after pump implantation, mice were treated with everolimus at 5 mg/kg/day per os 5 days a week.

On another occasion, 5 mice bearing large ~600 $mm^3$ MiaPaca2 tumours were implanted with subcutaneous Alzet micro-osmotic model 2002 pumps in the flank that delivered 3 mg/kg/day of PENAO. Four days later, mice were treated with 7.5 mg/kg/day PO of mTORC1 inhibitor, everolimus, for 7 days. Tumour volumes were calculated using the relationship length×height×width×0.523 and are expressed as relative tumour volumes, where the tumour volume at any given time is divided by the starting tumour volume. The mean of these values was used to calculate the ratio between control and treatment tumours as an indicator of drug efficacy. Tumour growth curves were compared using repeated measures two-way analysis of variance (ANOVA) using GraphPad Prism 6 (Tseng et al., 2010).

Control and treated tumours were fixed in formalin, embedded in paraffin and sections cut and stained with haematoxylin and eosin for the assessment of tumour necrosis. The percentage of tumour necrosis was measured using Genie Aperio Technologies LTD pattern-recognition software (Aperio Scanscope, Aperio Technologies LTD, Vista, Calif., USA) for the automated quantitative assessment of viable tumour tissue and necrosis (Beloueche-Babari et al., 2013). Changes in percentage of tumour necrosis were assessed with the Mann-Whitney test.

All analyses were performed using GraphPad Prism (GraphPad, San Diego, Calif.). All tests of statistical significance were two-sided and p values <0.05 were considered statistically significant.

Figure 4:
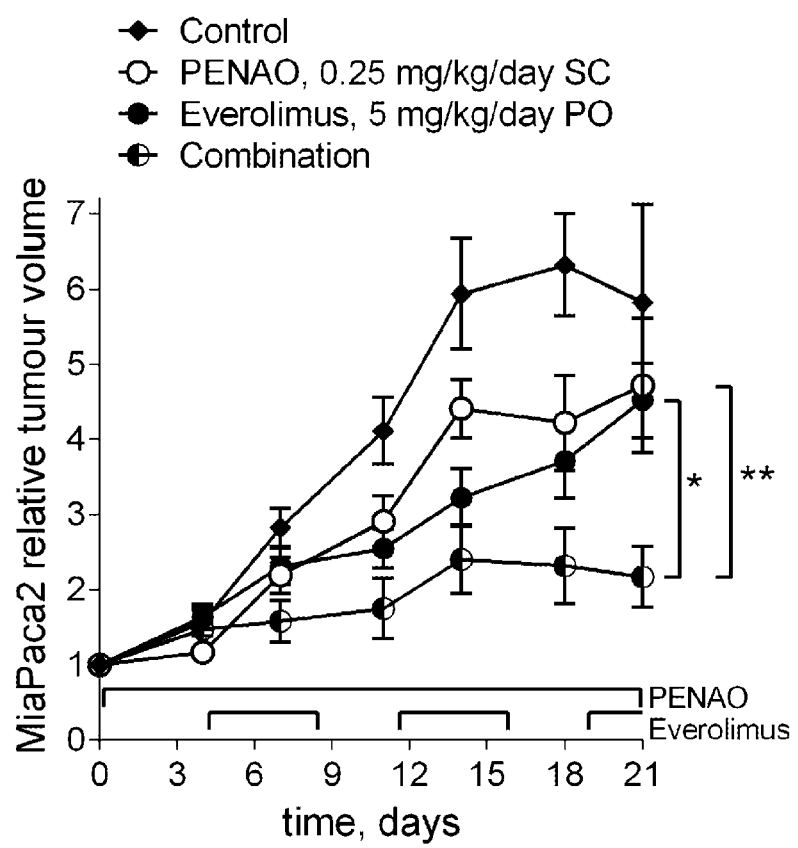
FIG. 4. Treatment with PENAO and rapalog results in synergistic inhibition of tumour growth. Subcutaneous human pancreatic MiaPaca2 tumours were established in the proximal midline of BALB/c nude mice. Mice bearing ~100 mm$^3$ tumours were randomized into four groups (n=8 per group) and implanted with subcutaneous (SC) micro-osmotic pumps in the flank that delivered vehicle or 0.25 mg/kg/day PENAO. Four days after pump implantation, mice were treated with 5 mg/kg/day everolimus per os (PO) for 5 days a week as indicated. Tumour volumes are expressed as relative tumour volumes, where the tumour volume at any given time is divided by the starting tumour volume. The data points and errors are the mean and SE of the tumour volumes. The tumour growth curves were compared using repeated measures two-way analysis of variance. *: p<0.05, **: p<0.01.

Results:
Treatment of human pancreatic tumours in immunocompromised mice with either PENAO or everolimus alone inhibited the rate of tumour growth (FIG. 4). There was a more profound inhibition of tumour growth when the compounds were administered at the same time. There was no sign or symptoms of toxicity in the treated mice.

Figure 5:
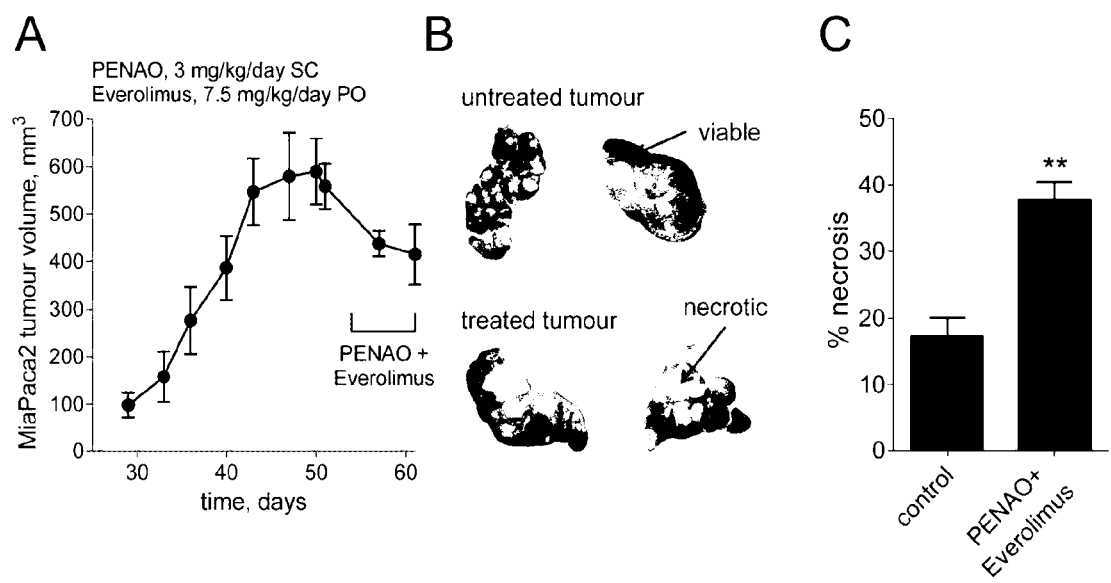
FIG. 5. Treatment with PENAO and rapalog results in tumour necrosis. A. Subcutaneous human pancreatic MiaPaca2 tumours were established in the proximal midline of BALB/c nude mice. After 50 days, 5 mice bearing large ~600 mm$^3$ tumours were implanted with subcutaneous (SC) micro-osmotic pumps in the flank that delivered 3 mg/kg/day of PENAO. At day 54, mice were treated with 7.5 mg/kg/day everolimus per os (PO) for 7 days. The data points and errors are the mean and SE of the tumour volumes. B. At day 61, tumours were excised, fixed then analysed for necrosis. Two representative tumour sections of each group are presented. Necrosis regions (blue) were quantified and compared with viable tumour regions (red) using Genie Aperio Technologies LTD pattern-recognition software. C. Quantification of tumour necrosis in control versus combination PENAO+everolimus treated tumours. The bars and errors are the mean and SD of the analysis of 2 sections per control (n=8) and treated (n=5) tumour. **: p<0.01.

Treatment of large human pancreatic tumours in immunocompromised mice with PENAO and everolimus at near maximal tolerated dose levels resulted in tumour necrosis (FIG. 5). There was no sign or symptoms of toxicity in the treated mice.

Treatment with PENAO and a rapalog results in synergistic inhibition of the rate of human tumour growth in mice and triggers tumour necrosis. The combination therapy is well tolerated, with no signs or symptoms of toxicity.

REFERENCES

Beloueche-Babari, M., Jamin, Y., Arunan, V., Walker-Samuel, S., Revill, M., Smith, P. D., Halliday, J., Waterton, J. C., Barjat, H., Workman, P., et al. (2013). Acute tumour response to the MEKI/2 inhibitor selumetinib (AZD6244, ARRY-142886) evaluated by non-invasive diffusion-weighted MRI. Br J Cancer 109, 1562-1569.

Chou, T (2010) Drug combination studies and their synergy quantification using the Chou-Talalay method. Cancer Res. 70(2) 440-446.

Dilda, P. J., Decollogne, S., Weerakoon, L., Norris, M. D., Haber, M., Allen, J. D., and Hogg, P. J. (2009). Optimization of the antitumor efficacy of a synthetic mitochondrial toxin by increasing the residence time in the cytosol. J Med Chem 52, 6209-6216.

Klionsky, D. J., Abdalla, F. C., Abeliovich, H., Abraham, R. T., Acevedo-Arozena, A., Adeli, K., Agholme, L., Agnello, M., Agostinis, P., Aguirre-Ghiso, J. A., et al. (2012). Guidelines for the use and interpretation of assays for monitoring autophagy. Autophagy 8, 445-544.

Lena, A., Rechichi, M., Salvetti, A., Bartoli, B., Vecchio, D., Scarcelli, V., Amoroso, R., Benvenuti, L., Gagliardi, R., Gremigni, V., et al. (2009). Drugs targeting the mitochondrial pore act as cytotoxic and cytostatic agents in temozolomide-resistant glioma cells. Journal of translational medicine 7, 13.

Park, D., Chiu, J., Perrone, G. G., Dilda, P. J., and Hogg, P. J. (2012). The tumour metabolism inhibitors GSAO and PENAO react with cysteines 57 and 257 of mitochondrial adenine nucleotide translocase. Cancer cell international 12, 11.

Ramsay, E. E., Hogg, P. J., and Dilda, P. J. (2011). Mitochondrial metabolism inhibitors for cancer therapy. Pharm Res 28, 2731-2744.

Roberts, D. J., and Miyamoto, S. (2015). Hexokinase II integrates energy metabolism and cellular protection: Akting on mitochondria and TORCing to autophagy. Cell Death Differ 22, 248-257.

Roberts, D. J., Tan-Sah, V. P., Ding, E. Y., Smith, J. M., and Miyamoto, S. (2014). Hexokinase-II positively regulates glucose starvation-induced autophagy through TORC1 inhibition. Mol Cell 53, 521-533.

Schenone, S., Brullo, C., Musumeci, F., Radi, M., and Botta, M. (2011). ATP-competitive inhibitors of mTOR: an update. Curr Med Chem 18, 2995-3014.

Tseng, J. C., Granot, T., DiGiacomo, V., Levin, B., and Meruelo, D. (2010). Enhanced specific delivery and targeting of oncolytic Sindbis viral vectors by modulating vascular leakiness in tumor. Cancer Gene Ther 17, 244-255.

Zaytseva, Y. Y., Valentino, J. D., Gulhati, P., and Evers, B. M. (2012). mTOR inhibitors in cancer therapy. Cancer Lett 319, 1-7.

The invention claimed is:

1. A method of treating a cellular proliferative disease in a vertebrate, the method comprising administering to the vertebrate a therapeutically effective amount of an organo-arsenoxide compound or a pharmaceutically acceptable salt thereof, and an mTOR inhibitor, or a pharmaceutically acceptable salt thereof, wherein the organo-arsenoxide compound, or the pharmaceutically acceptable salt thereof, is administered first, followed by the mTOR inhibitor, or the pharmaceutically acceptable salt thereof, wherein the organo-arsenoxide compound is 4-(N—(S-penicillaminy-lacetyl)amino)phenylarsinous acid (PENAO), or a pharmaceutically acceptable salt thereof, and the mTOR inhibitor is a rapalog.

2. The method of claim 1, wherein the rapalog is selected from the group consisting of everolimus, temsirolimus, deforolimus and zotarolimus.

3. The method of claim 1, wherein the rapalog is everolimus or temsirolimus.

4. The method of claim 1, wherein the rapalog is everolimus.

5. The method of claim 1, wherein the proliferative disease is a solid tumour.

6. The method of claim 5, wherein the solid tumour is selected from the group consisting of lung cancer; breast cancer; colorectal cancer; anal cancer; pancreatic cancer; prostate cancer; ovarian carcinoma; liver and bile duct carcinoma; esophageal carcinoma; non-Hodgkin's lymphoma; bladder carcinoma; carcinoma of the uterus; glioma, diffuse intrinsic pontine glioma, glioblastoma, medullablastoma, and other tumours of the brain; kidney cancer; cancer of the head and neck; cancer of the stomach; testicular cancer; germ cell tumour; neuroendocrine tumour; cervical cancer; oral cancer, carcinoids of the gastrointestinal tract, breast, and other organs; signet ring cell carcinoma; mesenchymal tumours including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma or a leiomysarcoma.

7. The method of claim 5, wherein the solid tumor is selected from pancreatic cancer, ovarian carcinoma and glioblastoma.

8. The method of claim 5, wherein the solid tumor is pancreatic cancer.

9. The method of claim 5, wherein the sold tumor is ovarian carcimoma.

10. The method of claim 5, wherein the solid tumor is glioblastoma.

* * * * *